(12) United States Patent
Strick

(10) Patent No.: US 7,772,213 B2
(45) Date of Patent: Aug. 10, 2010

(54) COMPOSITION FOR THE TREATMENT OF INFLAMMATORY CONDITIONS

(76) Inventor: Nathan Strick, 3243 Lawrence Ave., Oceanside, NY (US) 11572

( * ) Notice: Subject to any disclaimer, the term of this patent is extended or adjusted under 35 U.S.C. 154(b) by 839 days.

(21) Appl. No.: 11/494,722

(22) Filed: Jul. 27, 2006

(65) Prior Publication Data

US 2008/0027026 A1    Jan. 31, 2008

(51) Int. Cl.
    *A61K 31/70* (2006.01)
(52) U.S. Cl. ...................................................... 514/57
(58) Field of Classification Search .................. None
    See application file for complete search history.

(56) References Cited

U.S. PATENT DOCUMENTS

| | | | |
|---|---|---|---|
| 5,955,502 | A | 9/1999 | Hansen et al. |
| 6,165,493 | A | 12/2000 | Neurath et al. |
| 6,462,030 | B1 | 10/2002 | Neurath |
| 6,689,339 | B1 | 2/2004 | Tanaka et al. |
| 6,720,009 | B2 | 4/2004 | Gestrelius |
| 7,030,104 | B2 | 4/2006 | Gray et al. |
| 7,138,143 | B1 * | 11/2006 | Mukai et al. ........... 424/490 |
| 2002/0169105 | A1 | 11/2002 | Gestrelius |
| 2003/0152611 | A1 | 8/2003 | Illel et al. |
| 2003/0157187 | A1 | 8/2003 | Hunter |
| 2003/0219489 | A1 | 11/2003 | Curatolo et al. |
| 2004/0024036 | A1 | 2/2004 | Charlier et al. |
| 2004/0208906 | A1 | 10/2004 | Tatara et al. |
| 2005/0069591 | A1 | 3/2005 | Bernstein et al. |

FOREIGN PATENT DOCUMENTS

| | | |
|---|---|---|
| WO | WO 99/48477 | 9/1999 |
| WO | WO 2006/002365 | 1/2006 |

OTHER PUBLICATIONS

Neurath et al., "In Vitro Activity of a Cellulose Acetate . . . ", J. Antimicrob Chemother 2000, 713-714 (45); British Society for Antimicrobial Chemotherapy.
Neurath, "Microbicide for Prevention of Sexually Transmitted Diseases . . . ", Aids Patient Care and STD's, Nov. 4, 2000, pp. 215-219, vol. 14, No. 4, Mary Ann Liebert, Inc., N.Y.
Neurath et al., "A Microbicide for the Third Millenium", Biochemical Virology Laboratory, Kimball Research Institute, 2000, pp. 713-717, Monduzzi Editore S.p. A.—MEDIMOND,Inc.
Manson et al., "Effect of a Cellulose Acetate . . . ", Antimicrobial Agents and Chemotherapy, Nov. 2000, pp. 3199-3202, vol. 44, No. 11, American Society for Microbiology.
Kawamura et al., "Candidate Microbicides . . . ", Journal of Experimental Medicine, Nov. 20, 2000, 1491-1500, vol. 192, No. 10, [www.jem.org].
Neurath, et al., "Anti-HIV-1 Activity of anionic polymers . . . ", BMC Infectious Diseases, Nov. 2002, 2:27, Biomed Central Ltd.
Fichorova et al., "Anti-Human Immunodeficiency Virus Type 1 . . . ", Antimocrobial Agents and Chemotherapy, pp. 323-335, Jan. 2005, American Society for Microbiology.

* cited by examiner

*Primary Examiner*—Elli Peselev
(74) *Attorney, Agent, or Firm*—Gottlieb, Rackman & Reisman

(57) ABSTRACT

A novel treatment for topical inflammatory conditions such as acne, eczema, shingles, insect bites and hives is provided, consisting of the application of a pharmaceutical cream or ointment which incorporates hydroxypropyl methylcellulose acetate succinate ("HPMCAS") in a micronized form and which preferably contains one or more thickeners, a bioadhesive agent and water so that the formulation, when applied, can stick to the area to be treated.

17 Claims, No Drawings

COMPOSITION FOR THE TREATMENT OF INFLAMMATORY CONDITIONS

BACKGROUND OF THE INVENTION

The present invention relates to the treatment of inflammatory conditions, and more particularly to a formulation or composition for topical administration that is designed to treat itching due to inflammatory conditions such as acne, eczema, shingles, psoriasis, insect bites and hives.

Creams, gels and ointments, which can be administered easily and which are convenient in terms of portability, are used as preparations for topical administration in various diseases. For example, antibiotic creams are useful, particularly for topical inflammatory diseases due to infection with microorganisms. Antibiotic creams and ointments are less than desirable since they can lead to antibiotic resistance.

Another type of cream or ointment for treating acne and other topical inflammatory conditions include over-the-counter materials such as salicylic acid and benzoyl peroxide formulations. Such cream and ointment formulations are often unpleasant, irritating and are largely ineffective.

Accordingly, it would be desirable to provide an improved composition for treating topical inflammatory conditions.

SUMMARY OF THE INVENTION

Generally speaking, in accordance with the invention, it has been discovered that topical inflammatory conditions can be effectively treated with hydroxypropyl methylcellulose acetate succinate ("HPMCAS") in order to lessen or eliminate inflammation. In the inventive formulation, HPMCAS is in a micronized form, and preferably combined with one or more thickeners in order to form a pharmaceutical cream or ointment.

The inventive formulation should also include a bio-adhesive agent so that the formulation will stick to the skin of the patient for a substantial period of time. Suitable bio-adhesive agents include hydroxypropyl methylcellulose and methyl cellulose, with viscosity of 4,000 CPs. Other water soluble aliphatic ethers of cellulose with similar viscosity may also be suitable.

Accordingly, it is an object of the invention to provide an improved composition and treatment for topical inflammatory diseases. Another object of the invention is to provide an improved treatment for topical inflammatory diseases that is both effective and safe.

A further object of the invention is to provide an improved composition and treatment for topical and inflammatory conditions which is easy to carry out.

Other objects and advantages of the invention will, in part, be obvious and will, in part, be apparent from the following description.

DETAILED DESCRIPTION OF THE PREFERRED EMBODIMENT

The present invention provides a novel treatment for topical inflammatory conditions such as acne, eczema, shingles, psoriasis, insect bites and hives. The treatment consists of the application of a cream or ointment which incorporates micronized hydroxypropyl methylcellulose acetate succinate ("HPMCAS"). The cream or ointment is applied to the effected area on the skin.

The inventive cream is prepared by making a suspension of HPMCAS (either alone or with other ingredients, as described below) in water and mixing the two together. The weight percent of HPMCAS in the invention formulation (in the prepared suspension) is between about 15% and 50%, and more preferably between 15% and 25% by weight.

In addition to HPMCAS, the inventive cream or ointment formulation may also include one or more thickeners for the formulation to become thickened before application and to also prevent settling of the mixture. Suitable thickeners include polyethylene glycol and glycerol. The thickener should be present in the inventive formulation by weight in an amount between about 1.0% and 20%. The thickener should be one that maintains a relatively low pH (4.5-5.5) for the composition.

In addition, the inventive cream or ointment formulation should also include a bio-adhesive agent so that the formulation, when applied, sticks to the treated area. Suitable bio-adhesive agents include ethers of cellulose, such as hydroxypropyl methylcellulose and methyl cellulose. The bio-adhesive agent is present in the inventive composition in an amount between 1% and 3% by weight.

The inventive formulation also must include water in an amount between about 50% and 85% based on the total weight of the formulation.

The inventive formulation may also include one or more preservatives in an amount between about 0.02% and 0.1% based on the weight of the formulation. Examples of suitable preservatives include methyl paraben, propyl paraben, benzoic acid, sorbic acid and potassium sorbate.

It is important that the HPMCAS component of the inventive formulation be micronized so that it makes intimate contact with the skin. The HPMCAS should have a particle size of between about 0.1 microns and 10 microns in micronized form, preferably from 0.1 microns to 1.0 microns. A good source for HPMCAS to be used in the inventive formulation is AQOAT of the Japanese company Shin-etsu.

One advantage of the inventive formulation is that it incorporates HPMCAS, a high molecular weight and water insoluble polymer, in topical form. As a result, the HPMCAS does not penetrate into the skin cells of the patient.

The inventive formulation is prepared as follows:

The components listed below are added together and slowly mixed until they are hydrated. Thereafter, the components are rapidly mixed until a homogenous mixture is obtained.

An example of the inventive formulation is identified below:

| | |
|---|---|
| HPMCAS | 18% |
| glycerol | 20% |
| hydroxypropyl methylcellulose | 2% |
| methyl paraben | 0.10% |
| propyl paraben | 0.02% |
| potassium sorbate | 0.1% |

[Distilled water comprising the balance]

In tests, 16 patients were treated with a daily application of pharmaceutical creams containing HPMCAS in order to treat various inflammatory conditions, including eczema, psoriasis, acne, shingles, insect bites and other assorted skin condition. The results demonstrated that the patients exhibited substantially reduced symptoms; in some cases, the symptoms were totally eliminated.

It will thus be seen that the objects set forth above, and those made apparent from the preceding description are efficiently attained. Moreover, certain changes may be made to the inventive formulation without departing from the spirit and scope of the invention. It is intended that all matter contained in the above description shall be interpreted as illustrative and not in a limiting sense.

It will also be understood that the following claims are intended to cover all the generic and specific features of the invention herein described, and all statements of the scope of the invention which, as a matter of language, might be said to fall therebetween.

The invention claimed is:

1. A method for treating topical inflammatory conditions in a being comprising topically administering to said being a composition comprising a pharmaceutically effective amount of hydroxypropyl methylcellulose acetate succinate.

2. The method of claim 1, wherein said composition further includes a thickener and a bio-adhesive agent.

3. The method of claim 2, wherein said thickener is selected from the group consisting of polyethylene glycol and glycerol, and wherein said bio-adhesive agent is selected from the group consisting of hydroxypropyl methylcellulose and methyl cellulose.

4. The method of claim 2, wherein said composition further includes a preservative.

5. The method of claim 4, wherein said preservative is selected from the group consisting of methyl paraben, propyl paraben, potassium sorbate, sorbic acid and benzoic acid.

6. The method of claim 1, wherein the hydroxypropyl methylcellulose acetate succinate comprise particles in a micronized form.

7. The method of claim 1, wherein said composition includes hydroxypropyl methylcellulose acetate succinate in an amount between about 15 and 25 percent by weight.

8. The method of claim 1, wherein hydroxypropyl methylcellulose acetate succinate has a particle size of between about 0.1 and 10.0 μm.

9. A pharmaceutical composition for topical administration to a being comprising hydroxypropyl methylcellulose acetate succinate as the active ingredient in an amount between about 15 and 50 percent by weight, and a thickener in an amount between about 1.0 and 20.0 percent by weight.

10. The composition of claim 9, wherein said thickener is selected from the group consisting of glycerol and polyethylene glycol.

11. A pharmaceutical composition for topical administration to a being comprising hydroxypropyl methylcellulose acetate succinate as the active ingredient in an amount between about 15 and 50 percent by weight, and a bio-adhesive agent in an amount between about 1 and 3 percent by weight.

12. The composition of claim 11, wherein said bio-adhesive agent is selected from the group consisting of hydroxypropyl methylcellulose and methyl cellulose.

13. A pharmaceutical composition for topical administration to a being comprising hydroxypropyl methylcellulose acetate succinate as the active ingredient in an amount between about 15 and 50 percent by weight and a preservative.

14. The composition of claim 13, wherein said preservative is selected from the group consisting of methyl paraben, propyl paraben, potassium sorbate, sorbic acid and benzoic acid.

15. A pharmaceutical composition for topical administration to a being comprising hydroxvpropyl methylcellulose acetate succinate as the active ingredient in an amount between about 15 and 50 percent by weight,
   wherein the composition is in the form of a cream or ointment.

16. The method of claim 4, wherein the composition comprises:

| | |
|---|---|
| HPMCAS | 18% |
| glycerol | 20% |
| hydroxypropyl methylcellulose | 2% |
| methyl paraben | 0.10% |
| propyl paraben | 0.02% |
| potassium sorbate | 0.1% |

[Distilled water comprising the balance]

17. The composition of claim 9, the composition defined as follows:

| | |
|---|---|
| HPMCAS | 18% |
| glycerol | 20% |
| hydroxypropyl methylcellulose | 2% |
| methyl paraben | 0.10% |
| propyl paraben | 0.02% |
| potassium sorbate | 0.1% |

[Distilled water comprising the balance]

* * * * *